United States Patent
Yao et al.

(10) Patent No.: US 12,115,249 B2
(45) Date of Patent: Oct. 15, 2024

(54) AEROSOLIZABLE GEL

(71) Applicant: NICOVENTURES TRADING LIMITED, London (GB)

(72) Inventors: John Yao, Cambridge, MA (US); Joseph McLellan, Cambridge, MA (US); Xinhua Li, Cambridge, MA (US); Hootan Farhat, Cambridge, MA (US); Michael Bates, Cambridge, MA (US)

(73) Assignee: NICOVENTURES TRADING LIMITED, London (GB)

( * ) Notice: Subject to any disclaimer, the term of this patent is extended or adjusted under 35 U.S.C. 154(b) by 366 days.

(21) Appl. No.: 16/760,370

(22) PCT Filed: Oct. 31, 2018

(86) PCT No.: PCT/GB2018/053139
§ 371 (c)(1),
(2) Date: Apr. 29, 2020

(87) PCT Pub. No.: WO2019/086859
PCT Pub. Date: May 9, 2019

(65) Prior Publication Data
US 2021/0259300 A1    Aug. 26, 2021

(30) Foreign Application Priority Data
Nov. 1, 2017  (GB) ...................................... 1718031

(51) Int. Cl.
*A24B 15/167*    (2020.01)
*A61K 9/00*    (2006.01)
*A24F 40/10*    (2020.01)

(52) U.S. Cl.
CPC ............ *A61K 9/007* (2013.01); *A24B 15/167* (2016.11); *A24F 40/10* (2020.01)

(58) Field of Classification Search
CPC ............................. A24B 15/167; A61K 9/007
(Continued)

(56) References Cited

U.S. PATENT DOCUMENTS 4,946,853 A    8/1990  Bannon et al.
8,256,433 B2 *  9/2012  Gonda ................ A61M 15/009
                                                    131/270
(Continued)

FOREIGN PATENT DOCUMENTS

CN    105212273 A    1/2016
CN    104256888 B    6/2016
(Continued)

OTHER PUBLICATIONS

Biochemistry Stores Sigma Aldrich Non-Stocked Items, Sigma Aldrich Stocking Center, University of Iowa, https://medicine.uiowa.edu/biochemstores/sites/medicine.uiowa.edu.biochemstores/files/wysiwyg_uploads/Sigma%20Non-Stocked.pdf (Year: 2014).*
(Continued)

*Primary Examiner* — Russell E Sparks
(74) *Attorney, Agent, or Firm* — WOMBLE BOND DICKINSON (US) LLP

(57) ABSTRACT

There is provided an aerosolizable gel comprising (a) an active agent; (b) one or more gel forming materials, wherein the one or more gel forming materials is at least agarose, wherein the agarose is present in an amount of 1 to 12 wt. % based on the aerosolizable gel; (c) an aerosol forming material; and (d) water.

20 Claims, 4 Drawing Sheets

Figure 1:
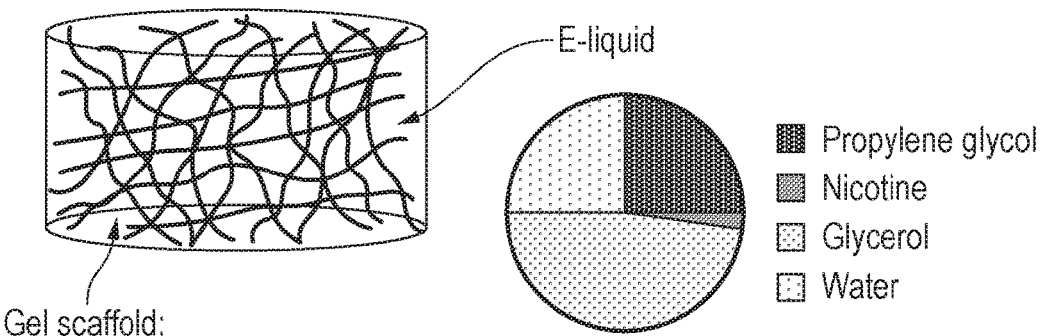

(58) Field of Classification Search
USPC .......................................................... 131/359
See application file for complete search history.

(56) References Cited

U.S. PATENT DOCUMENTS

| | | | |
|---|---|---|---|
| 8,881,737 B2* | 11/2014 | Collett | H05B 3/265 |
| | | | 131/194 |
| 10,660,365 B2* | 5/2020 | Lipowicz | A24F 40/20 |
| 2001/0031787 A1 | 10/2001 | Hsu et al. | |
| 2002/0170566 A1 | 11/2002 | Farr | |
| 2010/0329994 A1 | 12/2010 | Bayerl | |
| 2013/0192615 A1 | 8/2013 | Tucker et al. | |
| 2013/0298905 A1 | 11/2013 | Levin et al. | |
| 2015/0209530 A1 | 7/2015 | White | |
| 2015/0230515 A1 | 8/2015 | Lampe et al. | |
| 2015/0328415 A1 | 11/2015 | Minskoff et al. | |
| 2018/0029782 A1* | 2/2018 | Zuber | A24F 40/465 |

FOREIGN PATENT DOCUMENTS

| | | |
|---|---|---|
| WO | WO-9119746 A1 | 12/1991 |
| WO | WO-9524135 A1 | 9/1995 |
| WO | WO-9963951 A1 | 12/1999 |
| WO | WO-0028842 A1 | 5/2000 |
| WO | WO-03091315 A1 | 11/2003 |
| WO | WO-2006020166 A1 | 2/2006 |
| WO | WO-2006127772 A2 | 11/2006 |
| WO | WO-2011045609 A1 | 4/2011 |
| WO | WO-2012019372 A1 | 2/2012 |
| WO | WO-2014201432 A1 | 12/2014 |
| WO | WO-2015128665 A1 | 9/2015 |
| WO | WO-2015200049 A1 | 12/2015 |
| WO | WO-2016069876 A1 | 5/2016 |
| WO | WO-2016079589 A1 | 5/2016 |
| WO | WO-2018019578 A1 | 2/2018 |
| WO | WO-2018026400 A1 | 2/2018 |

OTHER PUBLICATIONS

International Preliminary Report on Patentability for Application No. PCT/GB2018/053139, mailed on Oct. 7, 2019, 13 pages.
International Search Report and Written Opinion for Application No. PCT/GB2018/053139, mailed on Feb. 19, 2012, 10 pages.

* cited by examiner

AEROSOLIZABLE GEL

CROSS-REFERENCE TO RELATED APPLICATIONS

The present application is a National Phase entry of PCT Application No. PCT/GB2018/053139, filed Oct. 31, 2018, which claims priority from Great Britain Patent Application No. 1718031.6 filed Nov. 1, 2017, each of which is fully incorporated herein by reference.

FIELD OF THE INVENTION

The present disclosure relates to an aerosolizable gel, a dosage form of an aerosolizable product, a method of forming an aerosol and to electronic vapor provision systems such as electronic delivery systems (e.g. e-cigarettes) incorporating said aerosolizable gel.

BACKGROUND TO THE INVENTION

Electronic vapor provision systems such as e-cigarettes generally contain a reservoir of liquid which is to be vaporized, typically containing active agent such as nicotine. When a user inhales on the device, a heater is activated to vaporize a small amount of liquid, which is therefore inhaled by the user.

The use of e-cigarettes in the UK has grown rapidly, and it has been estimated that there are now over a million people using them in the UK.

Current electronic cigarettes generate an aerosol by vaporizing a consumable e-liquid composed mostly of propylene glycol (PG), glycerol, water, active agent such as nicotine and flavors. The e-liquid is drawn by a wicking material into a resistive heating coil in which it is heated and evaporated. This straight-forward system suffers from a number of drawbacks such as leaking of the e-liquid though gaskets and the mouthpiece, inefficient heating and an inconsistent aerosol composition.

SUMMARY OF THE INVENTION

In one aspect there is provided an aerosolizable gel comprising
(a) an active agent;
(b) one or more gel forming materials, wherein the one or more gel forming materials is at least agarose, wherein the agarose is present in an amount of 1 to 12 wt. % based on the aerosolizable gel;
(c) an aerosol forming material; and
(d) water.

In one aspect there is provided a dosage form of an aerosolizable product, wherein the dosage form of the aerosolizable gel comprises
(a) an active agent, in an amount of 0.5 to 10 mg;
(b) one or more gel forming materials, wherein the one or more gel forming materials is at least agarose, wherein the agarose is present in an amount of 1 to 12 wt. % based on the aerosolizable gel;
(c) an aerosol forming material; and
(d) water.

In one aspect there is provided a method of forming an aerosol, the method comprising the step of heating an aerosolizable gel comprising
(a) an active agent;
(b) a gel forming material, wherein the gel forming material is at least agarose, wherein the agarose is present in an amount of 1 to 12 wt. % based on the aerosolizable gel;
(c) an aerosol forming material; and
(d) water.

In one aspect there is provided an electronic vapor provision system comprising:
(i) a vaporizer for vaporizing liquid for inhalation by a user of the electronic vapor provision system;
(ii) a power supply comprising a cell or battery for supplying power to the vaporizer
(iii) an aerosolizable gel comprising
(a) an active agent;
(b) a gel forming material, wherein the gel forming material is at least agarose, wherein the agarose is present in an amount of 1 to 12 wt. % based on the aerosolizable gel;
(c) an aerosol forming material; and
(d) water.

DETAILED DESCRIPTION

As discussed herein, an embodiment of the present invention provides an aerosolizable gel comprising (a) active agent; (b) one or more gel forming materials, wherein the one or more gel forming materials is at least agarose, wherein the agarose is present in an amount of 1 to 12 wt. % based on the aerosolizable gel; (c) an aerosol forming material; and (d) water.

We have found that we may avoid many of the limitations of the e-liquid of the prior art by using a non-liquid gel-medium. The use of a gel-medium allow for the aerosolizable active agent to be formed, patterned and stored in discrete doses. Discrete dosing allows for a consistent puff size, for consistent compositions and for efficient heating. Gel-media will also allow greater flexibility in the design of future heating technologies and consumable form factors. We have found that the present gel heats and vaporizes efficiently. We have also found that the gel consistently delivers active agent and flavors in the aerosol. In particular, the resulting aerosol does not contain any toxicants or malodor component resulting from the thermal degradation of the gel.

We have identified that selection of a particular gel forming material, namely one or more gel forming materials wherein the one or more gel forming materials is at least agarose and wherein the agarose is present in an amount of 1 to 12 wt. % based on the aerosolizable active agent gel, the problems of the prior art my may be overcome.

For ease of reference, these and further aspects of the present invention are now discussed under appropriate section headings. However, the teachings under each section are not necessarily limited to each particular section.

Active Agent

The aerosolizable gel comprises an active agent. By "active agent" it is meant an agent which has a biological effect on a subject when the aerosol is inhaled. The one or more active agents may be selected from nicotine, botanicals, and mixtures thereof. The one or more active agents may be of synthetic or natural origin. The active could be an extract from a botanical, such as from a plant in the tobacco family. An example active is nicotine.

In one aspect, the active agent is at least nicotine. Nicotine may be provided at any suitable amount depending on the desired dosage when inhaled by the user. In one aspect nicotine is present in an amount of no greater than 6 wt % based on the total weight of the aerosolizable nicotine gel. In one aspect nicotine is present in an amount of from 0.4 to 6 wt % based on the total weight of the aerosolizable nicotine gel. In one aspect nicotine is present in an amount of from 0.8 to 6 wt % based on the total weight of the aerosolizable nicotine gel. In one aspect nicotine is present in an amount of from 1 to 6 wt % based on the total weight of the aerosolizable nicotine gel. In one aspect nicotine is present in an amount of from 1.8 to 6 wt % based on the total weight of the aerosolizable nicotine gel. In one aspect nicotine is present in an amount of from 0.4 to 5 wt % based on the total weight of the aerosolizable nicotine gel. In one aspect nicotine is present in an amount of from 0.8 to 5 wt % based on the total weight of the aerosolizable nicotine gel. In one aspect nicotine is present in an amount of from 1 to 5 wt % based on the total weight of the aerosolizable nicotine gel. In one aspect nicotine is present in an amount of from 1.8 to 5 wt % based on the total weight of the aerosolizable nicotine gel. In one aspect nicotine is present in an amount of no greater than 4 wt % based on the total weight of the aerosolizable nicotine gel. In one aspect nicotine is present in an amount of from 0.4 to 4 wt % based on the total weight of the aerosolizable nicotine gel. In one aspect nicotine is present in an amount of from 0.8 to 4 wt % based on the total weight of the aerosolizable nicotine gel. In one aspect nicotine is present in an amount of from 1 to 4 wt % based on the total weight of the aerosolizable nicotine gel. In one aspect nicotine is present in an amount of from 1.8 to 4 wt % based on the total weight of the aerosolizable nicotine gel. In one aspect nicotine is present in an amount of no greater than 3 wt % based on the total weight of the aerosolizable nicotine gel. In one aspect nicotine is present in an amount of from 0.4 to 3 wt % based on the total weight of the aerosolizable nicotine gel. In one aspect nicotine is present in an amount of from 0.8 to 3 wt % based on the total weight of the aerosolizable nicotine gel. In one aspect nicotine is present in an amount of from 1 to 3 wt % based on the total weight of the aerosolizable nicotine gel. In one aspect nicotine is present in an amount of from 1.8 to 3 wt % based on the total weight of the aerosolizable nicotine gel. In one aspect nicotine is present in an amount of no greater than 1.9 wt % based on the total weight of the aerosolizable nicotine gel. In one aspect nicotine is present in an amount of no greater than 1.8 wt % based on the total weight of the aerosolizable nicotine gel. In one aspect nicotine is present in an amount of from 0.4 to 1.9 wt % based on the total weight of the aerosolizable nicotine gel. In one aspect nicotine is present in an amount of from 0.4 to 1.8 wt % based on the total weight of the aerosolizable nicotine gel. In one aspect nicotine is present in an amount of from 0.5 to 1.9 wt % based on the total weight of the aerosolizable nicotine gel. In one aspect nicotine is present in an amount of from 0.5 to 1.8 wt % based on the total weight of the aerosolizable nicotine gel In one aspect nicotine is present in an amount of from 0.8 to 1.9 wt % based on the total weight of the aerosolizable nicotine gel. In one aspect nicotine is present in an amount of from 0.8 to 1.8 wt % based on the total weight of the aerosolizable nicotine gel. In one aspect nicotine is present in an amount of from 1 to 1.9 wt % based on the total weight of the aerosolizable nicotine gel. In one aspect nicotine is present in an amount of from 1 to 1.8 wt % based on the total weight of the aerosolizable nicotine gel. In one aspect nicotine is present in an amount of less than 1.9 wt % based on the total weight of the aerosolizable nicotine gel. In one aspect nicotine is present in an amount of less than 1.8 wt % based on the total weight of the aerosolizable nicotine gel. In one aspect nicotine is present in an amount of from 0.4 to less than 1.9 wt % based on the total weight of the aerosolizable nicotine gel. In one aspect nicotine is present in an amount of from 0.4 to less than 1.8 wt % based on the total weight of the aerosolizable nicotine gel. In one aspect nicotine is present in an amount of from 0.5 to less than 1.9 wt % based on the total weight of the aerosolizable nicotine gel. In one aspect nicotine is present in an amount of from 0.5 to less than 1.8 wt % based on the total weight of the aerosolizable nicotine gel. In one aspect nicotine is present in an amount of from 0.8 to less than 1.9 wt % based on the total weight of the aerosolizable nicotine gel. In one aspect nicotine is present in an amount of from 0.8 to less than 1.8 wt % based on the total weight of the aerosolizable nicotine gel. In one aspect nicotine is present in an amount of from 1 to less than 1.9 wt % based on the total weight of the aerosolizable nicotine gel. In one aspect nicotine is present in an amount of from 1 to less than 1.8 wt % based on the total weight of the aerosolizable nicotine gel. In one aspect nicotine is present in an amount of no greater than 2 wt % based on the total weight of the aerosolizable nicotine gel. In one aspect nicotine is present in an amount of no greater than 1.8 wt % based on the total weight of the aerosolizable nicotine gel.

In the context of the present invention, reference to nicotine includes nicotine in both protonated form and in unprotonated form.

In one aspect the nicotine solution comprises nicotine in unprotonated form and nicotine in protonated form. In one aspect the nicotine solution comprises nicotine in unprotonated form and nicotine in monoprotonated form. Although it is envisaged that the solution will typically comprise nicotine in unprotonated form and nicotine in monoprotonated form, it may be that small amounts of diprotonated nicotine are present. In one aspect the nicotine solution comprises nicotine in unprotonated form, nicotine in monoprotonated form and nicotine in diprotonated form. As will be understood by one skilled in the art, the protonated form of nicotine is prepared by reacting unprotonated nicotine with an acid. The acids are one or more suitable acids. In one aspect the acid is an organic acid. In one aspect the acid is a carboxylic acid. The carboxylic acid may be any suitable carboxylic acid. In one aspect the acid is a mono-carboxylic acid. In one aspect the acid is selected from the group consisting of benzoic acid, levulinic acid, acetic acid, lactic acid, formic acid, citric acid, pyruvic acid, succinic acid, tartaric acid, oleic acid, sorbic acid, propionic acid, phenylacetic acid, and mixtures thereof.

Gel Forming Materials

As discussed herein the aerosolizable gel comprises one or more gel forming materials, wherein the one or more gel forming materials is at least agarose, wherein the agarose is present in an amount of 1 to 12 wt. % based on the aerosolizable gel. In one aspect agarose is present in an amount of 1 to 11 wt. % based on the total weight of the aerosolizable gel. In one aspect agarose is present in an amount of 1 to 10 wt. % based on the total weight of the aerosolizable gel. In one aspect agarose is present in an amount of 1 to 9 wt. % based on the total weight of the aerosolizable gel. In one aspect agarose is present in an amount of 1 to 8 wt. % based on the total weight of the aerosolizable gel. In one aspect agarose is present in an amount of 1 to 7 wt. % based on the total weight of the aerosolizable gel. In one aspect agarose is present in an amount of 1 to 6 wt. % based on the total weight of the aerosolizable gel. In one aspect agarose is present in an amount of 1 to 5 wt. % based on the total weight of the aerosolizable gel. In one aspect agarose is present in an amount of 1 to 4 wt. % based on the total weight of the aerosolizable gel. In one aspect agarose is present in an amount of 1 to 3 wt. % based on the total weight of the aerosolizable gel.

As will be appreciated by one skilled in the art, in one aspect the aerosolizable gel may contain other gel forming materials in addition to the agarose. In one aspect the aerosolizable gel contains no other gel forming materials in addition to the agarose. Thus in one aspect the aerosolizable gel comprises gel forming materials consisting of agarose.

In one aspect, wherein the one or more gel forming materials is present in an amount of 1 to 12 wt. % based on the aerosolizable gel. In one aspect the one or more gel forming materials is present in an amount of 1 to 11 wt. % based on the total weight of the aerosolizable gel. In one aspect the one or more gel forming materials is present in an amount of 1 to 10 wt. % based on the total weight of the aerosolizable gel. In one aspect the one or more gel forming materials is present in an amount of 1 to 9 wt. % based on the total weight of the aerosolizable gel. In one aspect the one or more gel forming materials is present in an amount of 1 to 8 wt. % based on the total weight of the aerosolizable gel. In one aspect the one or more gel forming materials is present in an amount of 1 to 7 wt. % based on the total weight of the aerosolizable gel. In one aspect the one or more gel forming materials is present in an amount of 1 to 6 wt. % based on the total weight of the aerosolizable gel. In one aspect the one or more gel forming materials is present in an amount of 1 to 5 wt. % based on the total weight of the aerosolizable gel. In one aspect the one or more gel forming materials is present in an amount of 1 to 4 wt. % based on the total weight of the aerosolizable gel. In one aspect the one or more gel forming materials is present in an amount of 1 to 3 wt. % based on the total weight of the aerosolizable gel.

When vaporizing gels on a hot surface we found that many of them suffered from poor thermal contact with the heating element. The e-liquid portion in immediate contact with the heater would evaporate leaving behind and insulating layer between the heater and the rest of the gel. We identified gels that melt upon heating, to maximize thermal contact between the e-liquid in the gel and the heating source. Agar was found to melt upon heating. Agar (containing agarose) is commonly used for making rigid aqueous gels in food products and for making gel electrophoresis plates used in molecular biology. Aqueous agar gels will set at temperatures below 35-40° ° C. and melt at temperatures above 85° C. Agar is a seaweed derived mixture of the polysaccharide agarose and the protein mixture, agaropectin. We have found that the gel strength of the composition may be optimized by use of agarose products in place of agar. Therefore, in one aspect the presence of agar is to be avoided or to be substantially avoided.

In one aspect, the aerosolizable gel contains agar in an amount of less than 0.1 wt. % based on the aerosolizable gel. In one aspect, the aerosolizable gel contains agar in an amount of less than 0.05 wt. % based on the aerosolizable gel. In one aspect, the aerosolizable gel contains agar in an amount of less than 0.01 wt. % based on the aerosolizable gel. In one aspect, the aerosolizable gel contains agar in an amount of less than 0.005 wt. % based on the aerosolizable gel. In one aspect, the aerosolizable gel contains agar in an amount of less than 0.001 wt. % based on the aerosolizable gel.

In one aspect, the aerosolizable gel contains agaropectin in an amount of less than 0.1 wt. % based on the aerosolizable gel. In one aspect, the aerosolizable gel contains agaropectin in an amount of less than 0.05 wt. % based on the aerosolizable gel. In one aspect, the aerosolizable gel contains agaropectin in an amount of less than 0.01 wt. % based on the aerosolizable gel. In one aspect, the aerosolizable gel contains agaropectin in an amount of less than 0.005 wt. % based on the aerosolizable gel. In one aspect, the aerosolizable gel contains agaropectin in an amount of less than 0.001 wt. % based on the aerosolizable gel.

As discussed herein, we have identified that the gel strength of the agarose containing gel is an important factor in the delivery of a commercially acceptable gel product. Therefore the selection of agarose to deliver the desired gel strength provides advantages over the systems of the prior art. Gel strength may be measured using a Shore OO durometer as described in the examples. In one aspect the agarose used in the present invention has a gel strength of at least 1500 when measured at 1 wt %. In one aspect the agarose used in the present invention has a gel strength of at least 1800 when measured at 1 wt %.

In one aspect the agarose used in the present invention has a gel strength of at least 2000 when measured at 1.5 wt %. In one aspect the agarose used in the present invention has a gel strength of at least 2500 when measured at 1.5 wt %. In one aspect the agarose used in the present invention has a gel strength of at least 3000 when measured at 1.5 wt %. In one aspect the agarose used in the present invention has a gel strength of at least 3200 when measured at 1.5 wt %.

Aerosol Forming Material

The aerosol forming material of the aerosolizable gel may be any suitable aerosol forming material such that the aerosolizable gel can be vaporized for use. In one aspect the aerosol forming material is selected from glycerol, propylene glycol and mixtures thereof. In one aspect the aerosol forming material is at least glycerol. In one aspect the aerosol forming material consists essentially of glycerol. In one aspect the aerosol forming material consists of glycerol. In one aspect the aerosol forming material is at least propylene glycol. In one aspect the aerosol forming material consists essentially of propylene glycol. In one aspect the aerosol forming material consists of propylene glycol. In one aspect the aerosol forming material is at least a mixture of propylene glycol and glycerol. In one aspect the aerosol forming material consists essentially of a mixture of propylene glycol and glycerol. In one aspect the aerosol forming material consists of a mixture of propylene glycol and glycerol.

The aerosol forming material of the aerosolizable gel may be present in any suitable amount. In one aspect the aerosol forming material is present in an amount of 1 to 98 wt % based on the aerosolizable gel. In one aspect the aerosol forming material is present in an amount of 5 to 98 wt % based on the aerosolizable gel. In one aspect the aerosol forming material is present in an amount of 10 to 98 wt % based on the aerosolizable gel. In one aspect the aerosol forming material is present in an amount of 20 to 98 wt % based on the aerosolizable gel. In one aspect the aerosol forming material is present in an amount of 30 to 98 wt % based on the aerosolizable gel. In one aspect the aerosol forming material is present in an amount of 40 to 98 wt % based on the aerosolizable gel. In one aspect the aerosol forming material is present in an amount of 50 to 98 wt % based on the aerosolizable gel. In one aspect the aerosol forming material is present in an amount of 50 to 95 wt % based on the aerosolizable gel. In one aspect the aerosol forming material is present in an amount of 50 to 80 wt % based on the aerosolizable gel. In one aspect the aerosol forming material is present in an amount of 60 to 98 wt % based on the aerosolizable gel. In one aspect the aerosol forming material is present in an amount of 70 to 98 wt % based on the aerosolizable gel. In one aspect the aerosol forming material is present in an amount of 80 to 98 wt % based on the aerosolizable gel. In one aspect the aerosol forming material is present in an amount of 90 to 98 wt % based on the aerosolizable gel. In one aspect the aerosol forming material is present in an amount of 1 to 90 wt % based on the aerosolizable gel. In one aspect the aerosol forming material is present in an amount of 5 to 90 wt % based on the aerosolizable gel. In one aspect the aerosol forming material is present in an amount of 10 to 90 wt % based on the aerosolizable gel. In one aspect the aerosol forming material is present in an amount of 20 to 90 wt % based on the aerosolizable gel. In one aspect the aerosol forming material is present in an amount of 30 to 90 wt % based on the aerosolizable gel. In one aspect the aerosol forming material is present in an amount of 40 to 90 wt % based on the aerosolizable gel. In one aspect the aerosol forming material is present in an amount of 50 to 90 wt % based on the aerosolizable gel. In one aspect the aerosol forming material is present in an amount of 60 to 90 wt % based on the aerosolizable gel. In one aspect the aerosol forming material is present in an amount of 70 to 90 wt % based on the aerosolizable gel. In one aspect the aerosol forming material is present in an amount of 80 to 90 wt % based on the aerosolizable gel.

Water

The aerosolizable gel further comprises water. The water may be present in any suitable amount. In one aspect water is present in an amount of 1 to 50 wt % based on the aerosolizable gel. In one aspect water is present in an amount of 5 to 50 wt % based on the aerosolizable gel. In one aspect water is present in an amount of 10 to 50 wt % based on the aerosolizable gel. In one aspect water is present in an amount of 20 to 50 wt % based on the aerosolizable gel. In one aspect water is present in an amount of 1 to 40 wt % based on the aerosolizable gel. In one aspect water is present in an amount of 5 to 40 wt % based on the aerosolizable gel. In one aspect water is present in an amount of 10 to 40 wt % based on the aerosolizable gel. In one aspect water is present in an amount of 20 to 40 wt % based on the aerosolizable gel. In one aspect water is present in an amount of 1 to 30 wt % based on the aerosolizable gel. In one aspect water is present in an amount of 5 to 30 wt % based on the aerosolizable gel. In one aspect water is present in an amount of 10 to 35 wt % based on the aerosolizable gel. In one aspect water is present in an amount of 10 to 30 wt % based on the aerosolizable gel. In one aspect water is present in an amount of 20 to 30 wt % based on the aerosolizable gel.

In one aspect the combined amount of aerosol forming material and water in the aerosolizable gel is from 1 to 98 wt % based on the aerosolizable gel. In one aspect the combined amount of aerosol forming material and water in the aerosolizable gel is 5 to 98 wt % based on the aerosolizable gel. In one aspect the combined amount of aerosol forming material and water in the aerosolizable gel is 10 to 98 wt % based on the aerosolizable gel. In one aspect the combined amount of aerosol forming material and water in the aerosolizable gel is 20 to 98 wt % based on the aerosolizable gel. In one aspect the combined amount of aerosol forming material and water in the aerosolizable gel is 30 to 98 wt % based on the aerosolizable gel. In one aspect the combined amount of aerosol forming material and water in the aerosolizable gel is 40 to 98 wt % based on the aerosolizable gel. In one aspect the combined amount of aerosol forming material and water in the aerosolizable gel is 50 to 98 wt % based on the aerosolizable gel. In one aspect the combined amount of aerosol forming material and water in the aerosolizable gel is 60 to 98 wt % based on the aerosolizable gel. In one aspect the combined amount of aerosol forming material and water in the aerosolizable gel is 70 to 98 wt % based on the aerosolizable gel. In one aspect the combined amount of aerosol forming material and water in the aerosolizable gel is 80 to 98 wt % based on the aerosolizable gel. In one aspect the combined amount of aerosol forming material and water in the aerosolizable gel is 90 to 98 wt % based on the aerosolizable gel. In one aspect the combined amount of aerosol forming material and water in the aerosolizable gel is 1 to 90 wt % based on the aerosolizable gel. In one aspect the combined amount of aerosol forming material and water in the aerosolizable gel is 5 to 90 wt % based on the aerosolizable gel. In one aspect the combined amount of aerosol forming material and water in the aerosolizable gel is 10 to 90 wt % based on the aerosolizable gel. In one aspect the combined amount of aerosol forming material and water in the aerosolizable gel is 20 to 90 wt % based on the aerosolizable gel. In one aspect the combined amount of aerosol forming material and water in the aerosolizable gel is 30 to 90 wt % based on the aerosolizable gel. In one aspect the combined amount of aerosol forming material and water in the aerosolizable gel is 40 to 90 wt % based on the aerosolizable gel. In one aspect the combined amount of aerosol forming material and water in the aerosolizable gel is 50 to 90 wt % based on the aerosolizable gel. In one aspect the combined amount of aerosol forming material and water in the aerosolizable gel is 60 to 90 wt % based on the aerosolizable gel. In one aspect the combined amount of aerosol forming material and water in the aerosolizable gel is 70 to 90 wt % based on the aerosolizable gel. In one aspect the combined amount of aerosol forming material and water in the aerosolizable gel is 80 to 90 wt % based on the aerosolizable gel. In one aspect the combined amount of aerosol forming material and water in the aerosolizable gel is 90 to 90 wt % based on the aerosolizable gel.

Further Components

The gel may also comprise flavoring components. As used herein, the terms "flavor" and "flavorant" refer to materials which, where local regulations permit, may be used to create a desired taste or aroma in a product for adult consumers. Thus, whilst it is acknowledged that some other functional components of the formulation may contain components that have a perceptible flavor or aroma, such components are not added for this purpose and as such are not considered to be a "flavor" or "flavorant" in the context of the present invention. Furthermore, it will be understood that "flavors" or "flavorants" may well composed of one or more individual compounds that together form an identifiable flavor. As such, reference here to "flavor" or "flavorant" includes both singular and multi-component flavors. They may include extracts (e.g. licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

Dosage Form

As discussed herein in one aspect, an embodiment of the present invention provides a dosage form of an aerosolizable product, wherein the dosage form of the aerosolizable gel comprises (a) active agent in an amount of 0.5 to 10 mg;
(b) one or more gel forming materials, wherein the one or more gel forming materials is at least agarose, wherein the agarose is present in an amount of 1 to 12 wt. % based on the aerosolizable gel;
(c) an aerosol forming material; and
(d) water.

In one aspect the active agent is present in an amount of 0.5 to 8 mg. In one aspect the active agent is present in an amount of 0.5 to 7 mg. In one aspect the active agent is present in an amount of 0.5 to 6 mg. In one aspect the active agent is present in an amount of 0.5 to 5 mg. In one aspect the active agent is present in an amount of 0.5 to 4 mg. In one aspect the active agent is present in an amount of 0.5 to 3 mg. In one aspect the active agent is present in an amount of 0.5 to 2 mg. In one aspect the active agent is present in an amount of 1 to 5 mg. In one aspect the active agent is present in an amount of 1 to 4 mg. In one aspect the active agent is present in an amount of 1 to 3 mg. In one aspect the active agent is present in an amount of 1 to 2 mg.

In one aspect nicotine is present in an amount of 0.5 to 10 mg. In one aspect nicotine is present in an amount of 0.5 to 8 mg. In one aspect nicotine is present in an amount of 0.5 to 7 mg. In one aspect nicotine is present in an amount of 0.5 to 6 mg. In one aspect nicotine is present in an amount of 0.5 to 5 mg. In one aspect nicotine is present in an amount of 0.5 to 4 mg. In one aspect nicotine is present in an amount of 0.5 to 3 mg. In one aspect nicotine is present in an amount of 0.5 to 2 mg. In one aspect nicotine is present in an amount of 1 to 5 mg. In one aspect nicotine is present in an amount of 1 to 4 mg. In one aspect nicotine is present in an amount of 1 to 3 mg. In one aspect nicotine is present in an amount of 1 to 2 mg.

Method

As discussed herein in one aspect, an embodiment of the present invention provides a method of forming an aerosol, the method comprising the step of heating an aerosolizable gel comprising (a) an active agent;
(b) a gel forming material, wherein the gel forming material is at least agarose, wherein the agarose is present in an amount of 1 to 12 wt. % based on the aerosolizable gel;
(c) an aerosol forming material; and
(d) water.

Electronic Vapor Provision System

The aerosolizable gel may be contained or delivered by any means.

Throughout the following description the term "e-cigarette" is used; however, this term may be used interchangeably with electronic vapor provision system. As discussed herein, the aerosolizable gel of the present invention is typically provided for the delivery of an active agent to or within an e-cigarette. The aerosolizable gel may be held within an e-cigarette or may be sold separately, for example as one unit doses, for subsequent use with or in an e-cigarette. In one aspect the aerosolizable gel is contained within an e-cigarette. Therefore in a further aspect the present invention provides an electronic vapor provision system comprising: (i) a vaporizer for vaporizing liquid for inhalation by a user of the electronic vapor provision system: (ii) a power supply comprising a cell or battery for supplying power to the vaporizer (iii) an aerosolizable gel comprising (a) an active agent; (b) a gel forming material, wherein the gel forming material is at least agarose, wherein the agarose is present in an amount of 1 to 12 wt. % based on the aerosolizable gel; (c) an aerosol forming material; and (d) water.

BRIEF DESCRIPTION OF THE DRAWINGS

Embodiments of the present invention will now be described in further detail by way of example only with reference to the accompanying figure in which:

FIG. 1: Gels are composed of gel forming scaffolds holding onto a base e-liquid.

FIG. 2*a:* 3% agarose gel moulded into 1 cm diameter disks.

FIG. 2*b*: Agarose gel melting and evaporating on a 250° C. hotplate.

FIG. 2*c*: Patterned agarose gel dots on a flexible substrate. Each dot contains the equivalent on a single e-liquid puff (0.1 mg of nicotine).

FIG. 3: Shore OO durometer measurements on agarose gels.

FIG. 4*a*: Time required to evaporate 99% of the e-liquid for various gels. Data collected using the rapid heating apparatus.

FIG. 4*b*: Current-voltage energy consumed while heating samples from FIG. 4*a*.

FIG. 5: Aerosol generation/collection apparatus.

FIG. 6: The GCMS chromatogram of aerosol collected from the e-liquid and from a 1% agarose gel. The water, propylene glycol, nicotine and glycerol peaks are labeled.

FIG. 7: TGA of agarose (A2929).

FIG. 8: Aerosol composition derived from GCMS peak areas.

Embodiments of the invention will now be described with reference to the following non-limiting examples.

EXAMPLES

Formulations

Base e-liquid:

Propylene glycol 25 wt. %

Water 25 wt. %

Nicotine 1.86 wt. %

Glycerol 48.14 wt. %

Agar/agarose gels, base e-liquid together with one of:

Sigma Aldrich A2929

Sigma Aldrich A0576

Sigma Aldrich A1296

| Gel wt. % Agar/Agarose | Mass e-liquid for 10 g gel | Mass Agar/Agarose for 10 g gel |
|---|---|---|
| 1% | 9.9 g | 0.1 g |
| 3% | 9.7 g | 0.3 g |
| 5% | 9.5 g | 0.5 g |

For 10 g batch sizes of gels, measure appropriate amounts of e-liquid and dry agarose powder. Add dry powder to e-liquid at room temperature. Shake or stir vigorously to mix. Heat to 80° C. in oil bath for 10-15 minutes (or until no suspended solids can be observed). Remove from heat, cool briefly to avoid loss of water vapor. Pour warm gel into moulds. Cool to ~4° C. in a refrigerator to fully set gel into mould.

The formulations described herein provided a gelled product comprising propylene glycol, nicotine, glycerol and water held together with a gel scaffold in the manner shown in FIG. 1.

Figure 2:
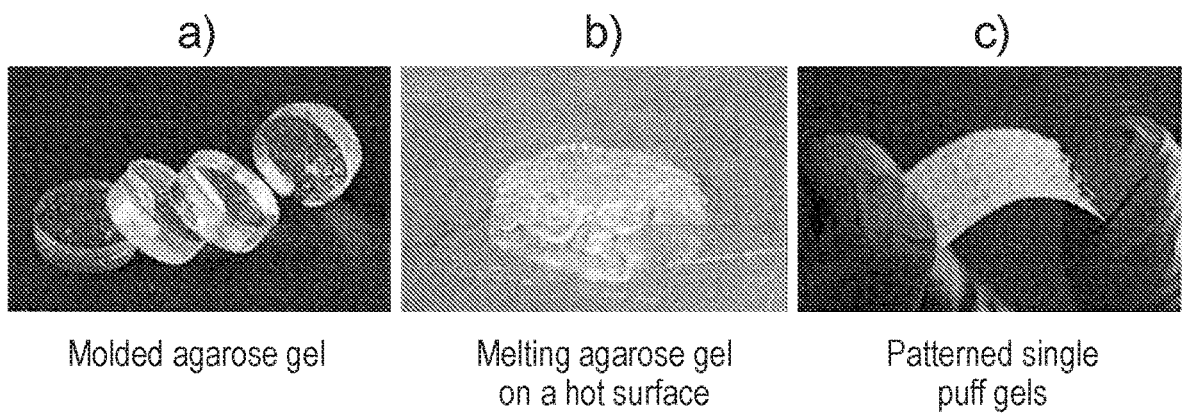
Figure 3:
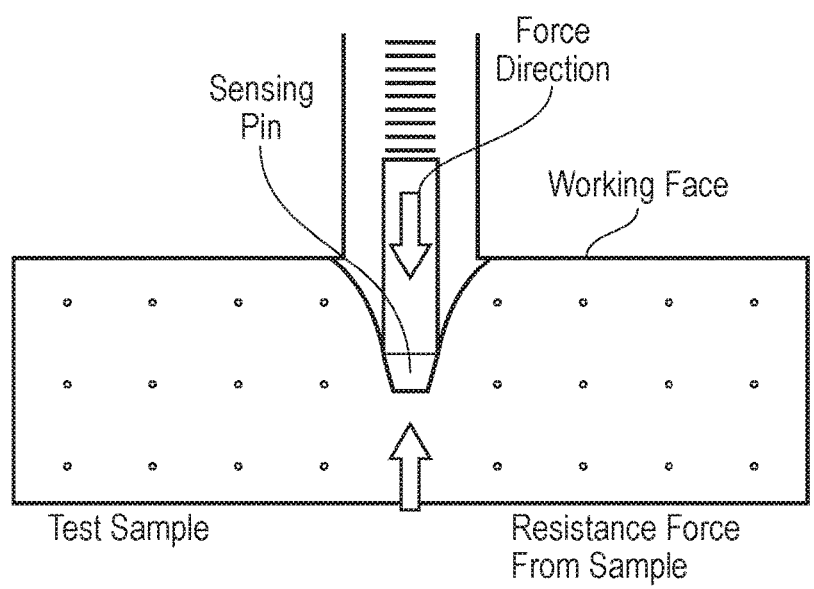

FIG. 2a shows agar gels that have retained shape of the moulds in which they were set. Upon heating to 250° C., agar gels first melt prior to the e-liquid component evaporating FIG. 2b. Gels were formed by dissolving agar in the e-liquid at 80° C. and allowing the gel to set upon cooling to room temperature. Agar loading levels as low as 0.5% gave free standing gels.

Table 1 summarizes the physical properties of some agarose grades sold by Sigma-Aldrich, available in a range of gel strengths and melting points. In addition to the initial agar (SA 1296), we made gels with high strength agaroses (SA 2929 and SA 0576) at loading levels between 0.2% and 8%. Gel strengths were characterized using a Shore durometer (Table 2). We found that formulations comprised of 1-3% of SA 2929 had the best balance of gel strength and minimum residue after vaporization. These gels were demonstrated in a number of form factors including discs, rods, and patterned single puff dots (FIG. 2c). The resulting gels were stable for over a month at room temperature Table 1: Various agarose products available from Sigma Aldrich and their properties. The bolded cells highlight the high gel strengths of the A2929 and A0576 products.

| Product | Gel Strength | Setting temperature | Melting temperature | Sulphate content |
|---|---|---|---|---|
| A2929 | >2000 @ 1% | 41 | NA | <0.20% |
| A0576 | >1800 @ 1%<br>>3200 @ 1.5% | 36 | 85 | <0.12% |
| A2576 | >100 @ 1%<br>>400 @ 1.5% | 17 | 60 | <0.14% |
| A9668 | >700 @ 1%<br>>1000 @ 1.5% | 35 | 87 | <0.30% |
| A7174 | >900 @ 1%<br>>1200 @ 1.5% | 41 | 95 | <0.20% |

Table 2: Shore 00 durometer measurements on agarose gels increasing loading of the A2929 and A0576. Asterisks indicated that gel was too soft to measure because it was punctured by the durometer probe.

| | 0.2% | 0.5% | 1% | 3% | 5% | 8% |
|---|---|---|---|---|---|---|
| Agar | Semi-liquid | * | * | 53 | 64 | 70 |
| A2929 | * | * | 35 | 66 | 69 | Viscous |
| A0576 | * | * | 35 | 68 | 75 | Viscous |

Testing Results:
Energy of Vaporization

For formulations with significant loading levels of additives, the added thermal mass of the additives should be considered. A crude estimate of the energy required to vaporize each formulation can be made by adding up the energy required to heat each component to its boiling point and the latent heat for each component to be vaporized. Despite only comprising 25% of the formulation, the water accounts for a significant portion of the energy require to vaporize the e-liquid.

Evaporation Kinetics:

The evaporation rate of the gels was determined gravimetrically by measuring the mass loss as a function of heating time. Initial measurements were performed by heating gel samples on hot plate—later, this was replaced by faster heating aerosol test rig. Sample sizes were chosen such that samples from the different formulations each contain the same mass of e-liquid (5-10 puff equivalents).

Figure 5:
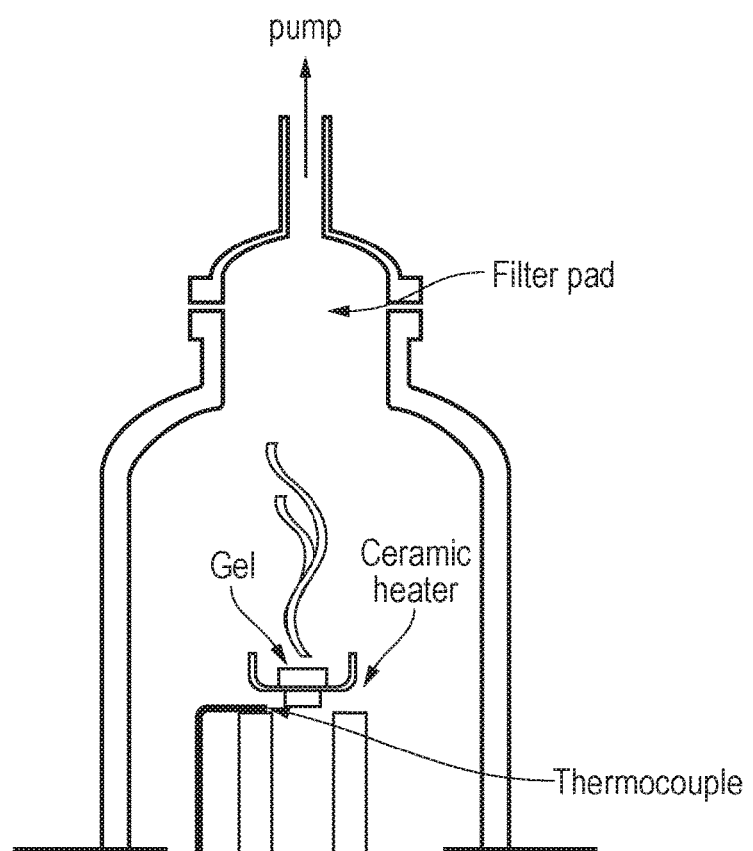

Aerosol test rig: In order to heat the gels on a time-scale closer to that of an e-cigarette device, we constructed a test rig for rapidly heating the gel and collecting the aerosol (FIG. 5). All subsequent evaporation rate measurements were performed on this device. The heating element (a ceramic disc resistive element) was used to heat samples in a 25 mg aluminum pan. A set-point of 300° C. can be reached within ~3-5 seconds. The heater sits in a glass chamber which is used to collect the aerosol onto a glass filter.

Figure 4A:
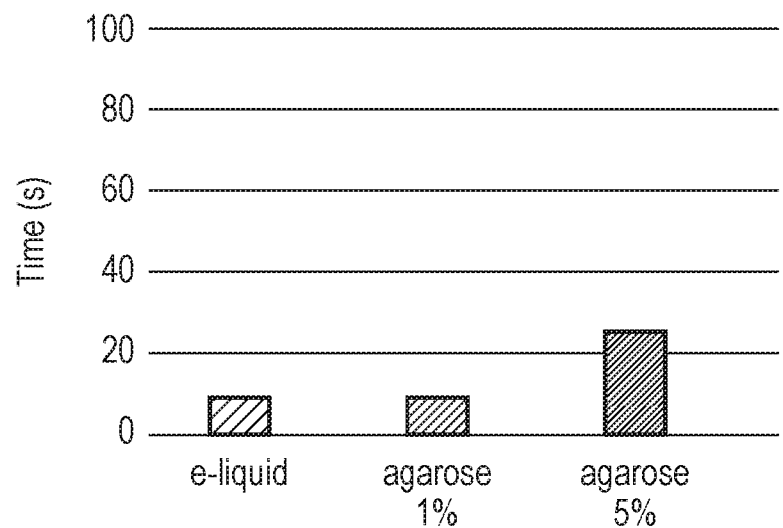
Figure 4B:
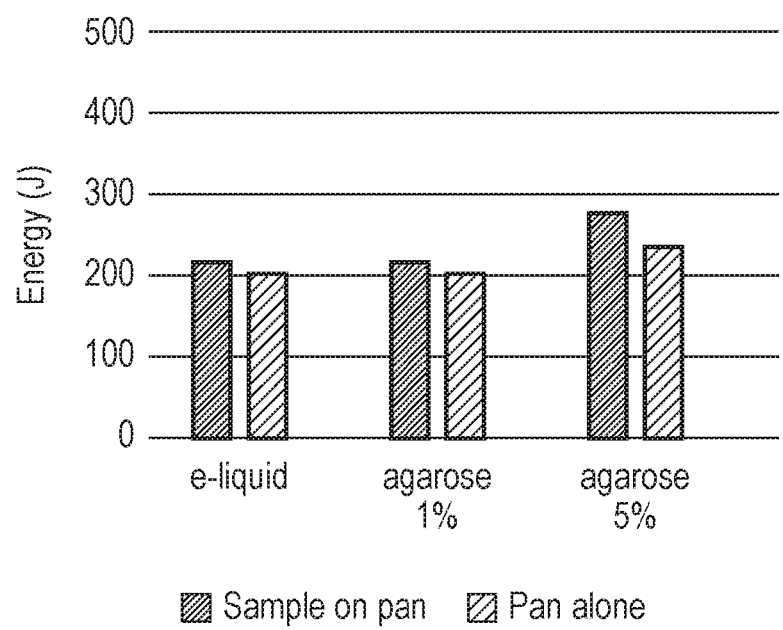

FIG. 4a shows the heating time and energy required to aerosolize four gels of interest: 1% agarose gel, and 5% agarose gel. The samples (5 puff equivalent) were heated to 300° C. and held for set durations. The change in sample mass was measured to determine the time required to vaporize 99% of the e-liquid in the sample. The results in FIG. 4a show that the 1 wt. % agar gel exhibited thermal properties nearly identical to the raw e-liquid. The 5 wt % gel sample required a 2.5 times longer heating duration. In addition to this gravimetric analysis, we also monitored power consumption to vaporize each sample and compared it to the energy required to heat the aluminum pan alone for that duration (FIG. 4b). The heat losses incurred during the longer heating cycle result in significantly more energy consumed. Based on these measurements, we found the agarose gels to be the most efficient at producing an aerosol and most similar in behavior to the base e-liquid.

Aerosol Extraction and GC/MS Analysis:

The composition of the aerosols generated from the five puff gel equivalents were analyzed by gas chromatography-mass spectrometry (GC/MS). The aerosol generated on the heating apparatus was collected onto a glass filter pad by evacuating the chamber with a vacuum pump. Deposits on the filter pad and on the chamber walls were extracted in methanol and analyzed.

The aerosol was collected by placing an inverted Sterlitech glass filtration apparatus (Cat. #311420) over the heater, with a Whatman 47 mm glass microfiber filter pad (Cat. #1821-047) attached to the apparatus to collect the aerosol. The filtration apparatus was connected to an Airpo pump (model #D2028B), with a maximum pump-rate of 12-15 LPM. The pump was set to begin running upon initiation of heating and to continue running for at least 10 seconds after the sample e-liquid was completely aerosolized. The filter was then placed in 10 mL of anhydrous methanol (Sigma-Aldrich Cat. #322415) in a 100 mL glass jar. The aerosol was extracted from the filter pad by gentle shaking of the jar for 30-60 sec. After initial extraction, the filter pad was removed from the methanol extraction solvent, squeezed to remove excess methanol and used to wipe the area around the sample holder pan and the exposed surfaces of the heating rig. The filter was then placed back in the methanol solvent to extract for another 30-60 sec, then removed from methanol, squeezed dry and used to wipe any remaining aerosol residue from the inside of the glass filtration apparatus. The filter pad was then placed back into the methanol solvent for a final 1-2 min of extraction, after which it was removed from the solvent, squeezed dry one final time and discarded. The methanol with the extracted aerosol was transferred into a 1 mL GC/MS vial with a rubber-septum cap and analyzed using an auto-liquid sampler attached to the Agilent 7820A GC with 5977E MSD. The GC/MS procedure used a DB-WAX GC column (30 m length, 0.25 mm diameter, 0.25 μm film thickness, Cat. #122-7032) for analyte separation. The procedure was optimized to resolve the peaks corresponding to: propylene glycol, nicotine and glycerol. The GC procedure is as follows:

| Parameter | Value |
|---|---|
| Oven: | |
| Initial Temp. | 50° C. |
| Rate | 30° C./min |
| Final Temp. | 260° C. |
| Final Hold Time | 2 min |
| Inlet: | |
| Temp. | 300° C. |
| Mode | Split |
| Split Ratio | 10:01 |
| Split Flow Rate | 20 mL/min |
| Pressure | 16.9 psi |
| Column: | |
| Model # | 122-7032 |
| Description | DB-WAX |
| Max Temp. | 260° C. |
| Length | 30 m |
| Diameter | 0.25 mm |
| Film Thickness | 0.25 μm |
| Mode | Constant Flow |
| Flow Rate | 2 mL/min |
| Average Velocity | 51.5 cm/sec |

To quantify the relative ratios of the e-liquid components, the peak areas from aerosol extraction results were compared to peak areas of a set of standards. The standards used to produce a calibration curve were made by diluting pure e-liquid in anhydrous methanol. The e-liquid was first diluted 100-fold by pipetting 100 uL of e-liquid into 9.9 mL of anhydrous methanol using micropipettes. The standards were then further diluted and labeled according to their nicotine content. The stock 1:100 dilution contained 1860 ppm nicotine and was used to make standards containing 10, 20, 30, 40 & 50 ppm nicotine. The anhydrous methanol was run as a blank, followed by the calibration curve standards. A fresh set of standards was made and analyzed for each series of extraction samples to ensure accurate calibration.

Figure 6:
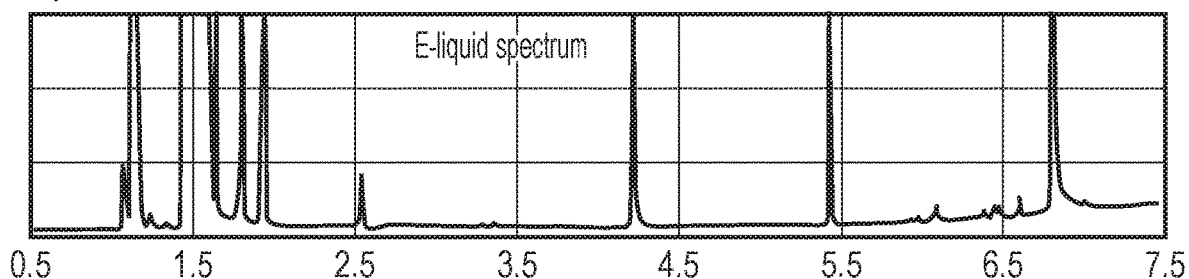
Figure 6:
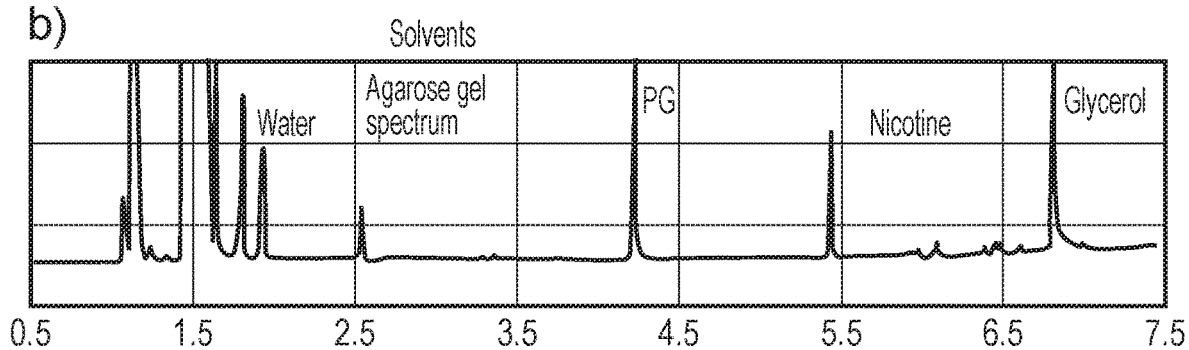
Figure 7:
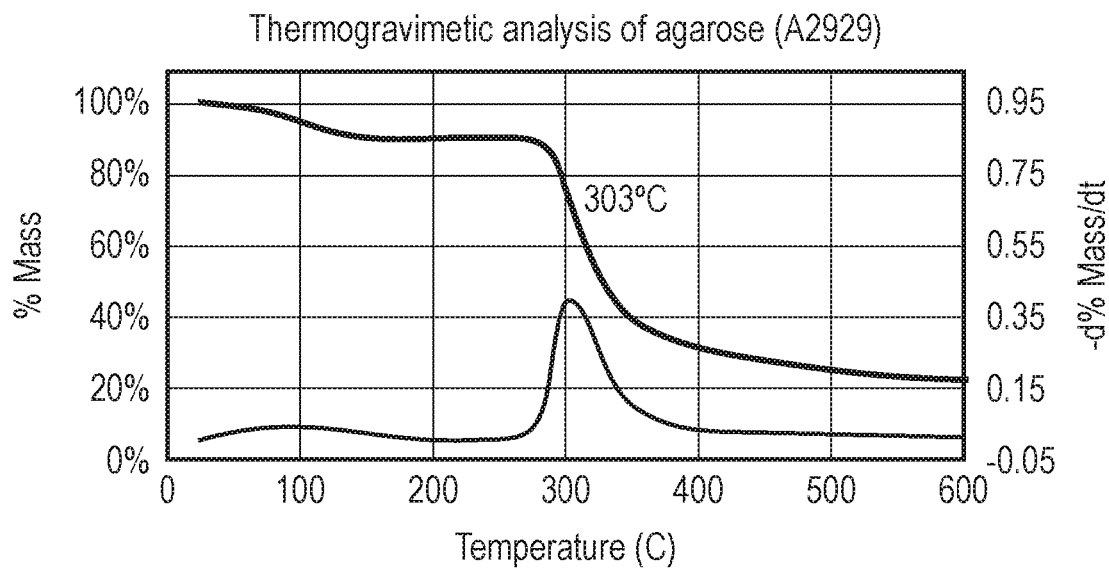

FIG. 6 shows the GC spectra aerosol collected from of the control e-liquid as well from a 1% agarose gel.

Figure 8:
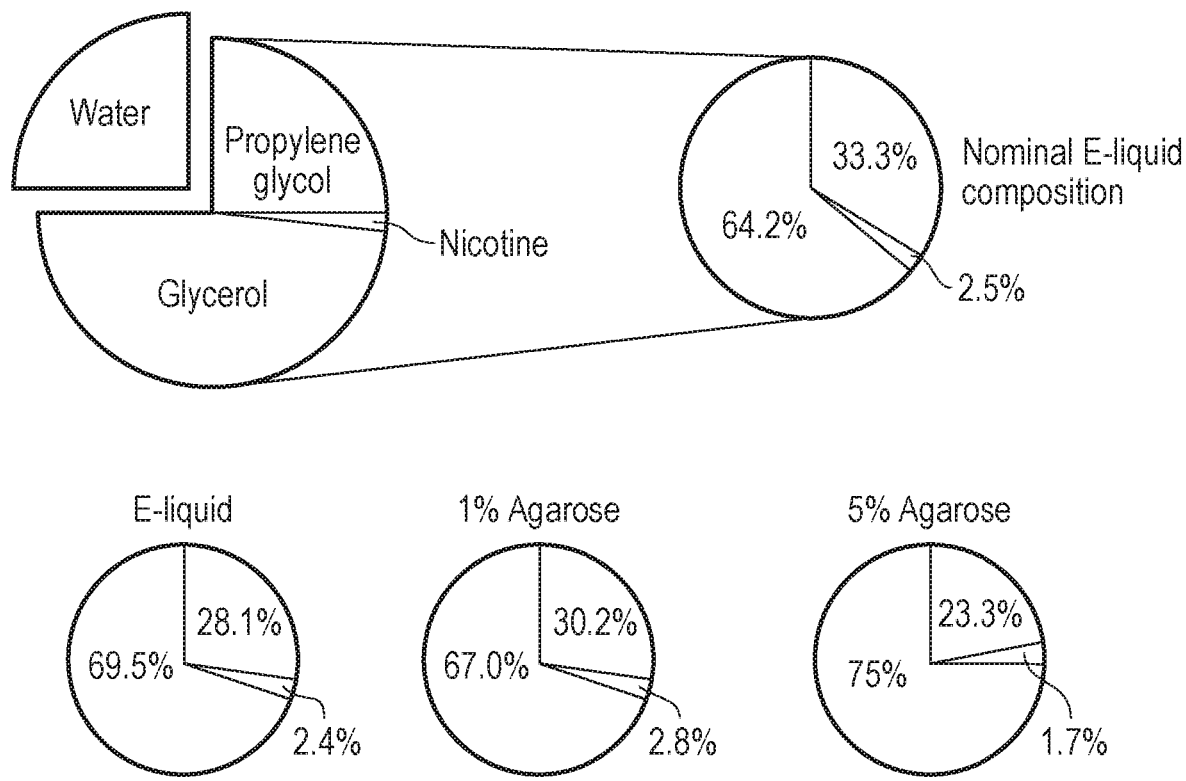

We found it challenging to quantify the water content of the aerosol due to varying amounts absorbed during the aerosol collection. The water absorption could not be accounted for by running a blank filter through the extraction process. We, therefore, focused on quantifying the relative compositions of the remaining three components of the aerosol. The results are presented in the form of pie-charts in FIG. 8. The compositions of the e-liquid and 1% agarose aerosols are very close to the nominal e-liquid composition. The 5%-agarose gels contain an increasing proportion of glycerol.

Thermal Stability of Additives:

Although the only volatile components of the formulated gels are the e-liquid components, compounds produced by thermal degradation of the gels could contribute volatile toxicants and undesirable flavor to the aerosol. Thermogravimetric analysis was performed on gel additives to characterize the temperature at which they decomposed and give-off volatile components. Thermogravimetric analysis on the dry powder gel additives was performed using a Shimadzu TGA-50. Each sample weighed 15-20 mg and were heated in an open aluminum pan (VWR 12577-060). The additives were heated to 600° ° C. at a rate of 20° C./min in an air atmosphere at a flow rate of 100 mL/min. Combined thermogravimetric analysis and differential scanning calorimetry were performed of fully formulated gels using a TA Instruments Q600. The samples were placed in covered alumina pans and an identical covered alumina pan was used for the DSC reference. Simultaneous TGA and DSC data was collected analyzed by heating to 400° C. at 10° C./min with a gas flow rate of 100 mL/min air.

Agarose had the highest onset temperature. For device with temperatures regulated to a maximum of 250° C., we do not expect significant volatile thermal and oxidative degradation products in the aerosol using this additive.

Agarose gels were also found to have the favorable property of being thermally reversible, allowing the gel to melt prior to evaporation. Very low agarose levels are needed to achieve rigid gels that can be moulded and patterned. At such low loading levels, the agarose gels vaporize nearly identically to the e-liquid, which is not surprising considering that they are 95-99% e-liquid. Further, at these loading levels, processing is efficient since the agarose can be directly incorporated with liquid component, without the need to dilute and remove water.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A dosage form of an aerosolizable gel comprising:
    (a) nicotine in an amount of 0.5 mg to 10 mg;
    (b) one or more gel forming materials, wherein the one or more gel forming materials is at least agarose, wherein the agarose is present in an amount of 1 to 3 wt. % based on the aerosolizable gel, and wherein the agarose has a gel strength of at least 1500 as measured using a Shore 00 durometer when measured at 1 wt %;

(c) an aerosol forming material; and
(d) water;
wherein the aerosolizable gel contains agaropectin in an amount of less than 0.1 wt. % based on the aerosolizable gel,
wherein the aerosolizable gel contains agar in an amount of less than 0.1 wt. % based on the aerosolizable gel,
wherein the aerosolizable gel is in a form of single puff dots, and
wherein the aerosolizable gel contains protonated nicotine.

2. The dosage form of the aerosolizable gel according to claim 1 wherein the nicotine is in an amount of no greater than 2 wt % based on the total weight of the aerosolizable gel.

3. The dosage form of the aerosolizable gel according to claim 1 wherein the nicotine is present in an amount of no greater than 1.8 wt % based on the total weight of the aerosolizable gel.

4. The dosage form of the aerosolizable gel according to claim 1 wherein the one or more gel forming materials is present in an amount of 1 to 12 wt. % based on the aerosolizable gel.

5. The dosage form of the aerosolizable gel according to claim 1 wherein the one or more gel forming materials is present in an amount of 1 to 8 wt. % based on the aerosolizable gel.

6. The dosage form of the aerosolizable gel according to claim 1 wherein the agarose has a gel strength of at least 1800 as measured using a Shore 00 durometer when measured at 1 wt %.

7. The dosage form of the aerosolizable gel according to claim 1 wherein the aerosolizable gel contains agar in an amount of less than 0.1 wt. % based on the aerosolizable gel.

8. The dosage form of the aerosolizable gel according to claim 1 wherein the aerosolizable gel contains agaropectin in an amount of less than 0.05 wt. % based on the aerosolizable gel.

9. The dosage form of the aerosolizable gel according to claim 1 wherein the aerosol forming material is selected from glycerol, propylene glycol and mixtures thereof.

10. The dosage form of the aerosolizable gel according to claim 1 wherein the aerosol forming material is a combination of glycerol and propylene glycol.

11. The dosage form of the aerosolizable gel according to claim 1 wherein the aerosol forming material is present in an amount of 50 to 95 wt. % based on the aerosolizable gel.

12. The dosage form of the aerosolizable gel according to claim 1 wherein the aerosol forming material is present in an amount of 50 to 80 wt. % based on the aerosolizable gel.

13. The dosage form of the aerosolizable gel according claim 1 wherein the water is present in an amount of 1 to 40 wt. % based on the aerosolizable gel.

14. The dosage form of the aerosolizable gel according to claim 1 wherein the water is present in an amount of 10 to 35 wt. % based on the aerosolizable gel.

15. The dosage form of the aerosolizable gel according to claim 1 wherein the nicotine is in an amount of 0.5 to 5 mg.

16. The dosage form of the aerosolizable gel according to claim 1 wherein the nicotine is in an amount of 1 to 3 mg.

17. The dosage form of an aerosolizable gel according to claim 1 wherein the aerosolizable gel contains protonated and unprotonated nicotine.

18. The dosage form of an aerosolizable gel according to claim 1 wherein the nicotine is protonated with an acid, wherein the acid is selected from the group consisting of benzoic acid, levulinic acid, acetic acid, lactic acid, formic acid, citric acid, pyruvic acid, succinic acid, tartaric acid, oleic acid, sorbic acid, propionic acid, phenylacetic acid, and mixtures thereof.

19. The dosage form of an aerosolizable gel according to claim 18 wherein the acid is selected from the group consisting of benzoic acid, acetic acid, formic acid, citric acid, tartaric acid, oleic acid, sorbic acid, propionic acid, phenylacetic acid, and mixtures thereof.

20. A dosage form of an aerosolizable gel comprising:
(a) nicotine in an amount of 0.5 to 10 mg;
(b) one or more gel forming materials, wherein the one or more gel forming materials is at least agarose, wherein the agarose is present in an amount of 1 to 3 wt. % based on the aerosolizable gel;
(c) an aerosol forming material; and
(d) water;
wherein the aerosolizable gel contains agar in an amount of less than 0.1 wt. % based on the aerosolizable gel, and
wherein the aerosolizable gel contains protonated nicotine.

* * * * *